US009709499B1

(12) United States Patent
Crafton et al.

(10) Patent No.: US 9,709,499 B1
(45) Date of Patent: Jul. 18, 2017

(54) MEASUREMENT OF OXYGEN

(71) Applicants: Jimmy W. Crafton, Waynesville, OH (US); Robert A. Forlines, Beavercreek, OH (US); Larry P. Goss, Beavercreek, OH (US); Stephen J. Palluconi, Dayton, OH (US); Jessica R. Webb, Waynesville, OH (US); Nikolay Rogoshchenkov, Centerville, OH (US); Grant R. McMillan, Beavercreek, OH (US)

(72) Inventors: Jimmy W. Crafton, Waynesville, OH (US); Robert A. Forlines, Beavercreek, OH (US); Larry P. Goss, Beavercreek, OH (US); Stephen J. Palluconi, Dayton, OH (US); Jessica R. Webb, Waynesville, OH (US); Nikolay Rogoshchenkov, Centerville, OH (US); Grant R. McMillan, Beavercreek, OH (US)

(73) Assignee: Innovative Scientific Solutions, Inc., Dayton, OH (US)

( * ) Notice: Subject to any disclaimer, the term of this patent is extended or adjusted under 35 U.S.C. 154(b) by 210 days.

(21) Appl. No.: 14/484,870

(22) Filed: Sep. 12, 2014

Related U.S. Application Data

(60) Provisional application No. 61/877,022, filed on Sep. 12, 2013.

(51) Int. Cl.
*G01N 21/64* (2006.01)

(52) U.S. Cl.
CPC ..... *G01N 21/643* (2013.01); *G01N 2021/6432* (2013.01); *G01N 2201/0627* (2013.01); *G01N 2201/13* (2013.01)

(58) Field of Classification Search
CPC ............... G01N 2021/6432; G01N 21/6408
See application file for complete search history.

(56) References Cited

U.S. PATENT DOCUMENTS 4,224,113 A * 9/1980 Kimura ............ G01N 27/4071
204/425
5,572,031 A 11/1996 Cooper et al.
(Continued)

FOREIGN PATENT DOCUMENTS

WO   2011020983 A2   2/2011

*Primary Examiner* — Yara B Green
(74) *Attorney, Agent, or Firm* — Stevens & Showalter LLP

(57) ABSTRACT

An oxygen number density or concentration sensor including a sampling luminescent oxygen probe located in a fluid environment, and a gas impermeable enclosure located in the fluid environment and a reference luminescent oxygen probe located within the gas impermeable enclosure, wherein the sampling and reference luminescent oxygen probes are formed by an ideal PSP. A predetermined fixed oxygen number density or concentration is provided within a medium contained in the gas impermeable enclosure. A detector receives signals corresponding to luminescent emissions of the sampling and reference probes. A processor determines a number density or concentration of oxygen in the fluid environment from a signal generated at the sampling probe with reference to an oxygen number density or concentration dependent signal generated at the reference probe.

18 Claims, 6 Drawing Sheets

(56) References Cited

U.S. PATENT DOCUMENTS

| | | | |
|---|---|---|---|
| 5,965,642 A * | 10/1999 | Gouterman | C08K 5/0091 |
| | | | 524/88 |
| 6,136,267 A | 10/2000 | Bergman | |
| 6,634,598 B2 | 10/2003 | Susko | |
| 6,904,930 B2 | 6/2005 | Susko | |
| 6,912,050 B2 * | 6/2005 | Inberg | G01N 21/6408 |
| | | | 250/458.1 |
| 7,231,809 B2 | 6/2007 | Susko | |
| 7,352,464 B2 | 4/2008 | Chen et al. | |
| 8,852,512 B2 * | 10/2014 | Lam | F02M 21/12 |
| | | | 422/400 |
| 2003/0116679 A1 * | 6/2003 | Susko | B64D 37/32 |
| | | | 244/135 R |
| 2005/0166660 A1 * | 8/2005 | Ammann | G01N 27/4165 |
| | | | 73/1.01 |
| 2006/0171845 A1 * | 8/2006 | Martin | B64D 37/32 |
| | | | 422/82.07 |
| 2007/0141695 A1 | 6/2007 | Mitchell | |
| 2011/0244592 A1 * | 10/2011 | Arzhakova | G01N 21/643 |
| | | | 436/164 |
| 2012/0097270 A1 | 4/2012 | Susko | |

\* cited by examiner

MEASUREMENT OF OXYGEN

CROSS REFERENCE TO RELATED APPLICATION

This application claims the benefit of U.S. Provisional Patent Application Ser. No. 61/877,022, filed Sep. 12, 2013, entitled "MEASUREMENT OF OXYGEN", the entire disclosure of which is incorporated by reference herein.

FIELD OF THE INVENTION

The present invention relates to monitoring a characteristic of fluids and, more particularly, to monitoring the number density, partial pressure or concentration of oxygen in a fluid.

BACKGROUND OF THE INVENTION

The number density, partial pressure or concentration of oxygen may be monitored in a gas or fluid, or in the space above a fluid in a tank or container for various reasons. For example, the concentration of oxygen may be monitored in a fuel tank as part of a fuel inerting system for avoiding or minimizing the possibility of combustion in the fuel tank.

Fuel tank inerting systems have long been used in tactical aircraft, but are typically restricted to open-loop operation. While open-loop inerting systems provide an effective method of inerting the ullage in a fuel tank, such systems are implemented at a cost of higher demands on the propulsion and environmental systems for bleed air and power, and reduced life of the On-board Inert Gas Generation System (OBIGGS). Due to the highly combustible nature of the ullage environment of tactical aircraft, there is an associated requirement that a highly accurate oxygen sensor be used to monitor the ullage to ensure that the concentration of oxygen in the ullage does not exceed a predetermined maximum level. Further, inexpensive, compact oxygen sensors that may be effective for less volatile closed-loop automotive and industrial applications generally are not compatible with the highly combustible ullage environment of a tactical aircraft. This intrinsic safety requirement generally limits OBIGGS systems to open-loop operations, whether applied to military or commercial aircraft.

SUMMARY OF THE INVENTION

In accordance with an aspect of the invention, an oxygen number density, partial pressure, or concentration sensor is provided in a fluid environment. The sensor includes a sampling luminescent oxygen probe located in the fluid environment, and a gas impermeable enclosure located in the fluid environment and a reference luminescent oxygen probe located within the gas impermeable enclosure, wherein the sampling and reference luminescent oxygen probes are formed by an ideal PSP. A predetermined fixed oxygen number density, partial pressure, or concentration is provided within a medium contained in the gas impermeable enclosure, the oxygen number density, partial pressure or concentration within the gas impermeable enclosure being greater than 0% and less than or equal to a predetermined limit. An illumination source providing light energy to the sampling probe and the reference probe. A detector is provided to receive signals corresponding to luminescent emissions of the sampling and reference probes. A processor determines a number density, partial pressure, or concentration of oxygen in the fluid environment from a signal generated at the sampling probe with reference to an oxygen number density, partial pressure, or concentration dependent signal generated at the reference probe.

The processor can mix the signals from the sampling and reference probes to identify the number density, partial pressure, or concentration of oxygen in the fluid environment based on a measurement of the luminescent lifetime, or phase lag between the signals from the sampling and reference probes.

The illumination source can include a red LED and a blue or UV LED, and the red and blue/UV LEDs can provide light energy to both the sampling and the reference probes and wherein the blue/UV LED may be used to create a fluorescent emission from the sampling and reference probes that passes through a long-pass filter corresponding an oxygen quenching at each of the probes, and the red LED may provide a reflected light signal from the sampling and reference probes that is transmitted to the detector through a long-pass filter to establish and eliminate a system phase lag not associated with fluorescence from the sampling and reference probes.

A sampling channel can be provided from the sampling probe to the detector and a reference channel can be provided from the reference probe to the detector, each of the sampling channel and the reference channel can include a shutter for selectively controlling passage of signals from the sampling and reference probes to the detector.

The illumination source can include a pulsed Laser that can provide light energy to both the sampling and the reference probes to create a fluorescent emission from the sampling and reference probes that passes through a long-pass filter and these fluorescent signals can be detected and converted to lifetime using a variety of schemes including two-gate lifetime detection and digitizing and curve fitting the decay. The lifetime corresponding to an oxygen quenching from the reference probe is then used as a calibration point for the oxygen number density measurement of the sampling probe.

The reference cell can comprise a variable volume cell that varies a pressure within the gas impermeable enclosure to equilibrate to a pressure in the fluid environment. This provides the ability to create a reference probe with a fixed oxygen concentration, rather than a fixed number density or partial pressure.

The sensor can include at least two reference luminescent oxygen probes enclosed in separate gas impermeable enclosures, each of the gas impermeable enclosures containing oxygen at respective different number density, partial pressures, or concentrations and used as a reference for the signal generated at the sampling probe. A first of the reference probes can be at a first number density, partial pressure, or concentration for triggering a system to change the oxygen number density, partial pressure, or concentration in the fluid environment, and a second of the reference probes can be at a second number density, partial pressure, or concentration for triggering the system to discontinue changing the oxygen number density, partial pressure, or concentration in the fluid environment.

The illumination source can include an LED or pulsed Laser provided to each of the sampling probe and the reference probe, and the detector can include a first detector receiving a luminescent emission of the sampling probe, and a second detector receiving a luminescent emission of the reference probe.

In accordance with another aspect of the invention, a method of sensing an oxygen level in a fluid environment is provided. The method comprises obtaining a sampling signal from a sampling luminescent oxygen probe located in the fluid environment; obtaining a reference signal from a reference luminescent oxygen probe located within a gas impermeable enclosure positioned in the fluid environment, wherein the sampling and reference luminescent oxygen probes are formed by an ideal PSP; providing a light source modulated at a predetermined frequency to the sampling and reference probes; receiving the sampling and reference signals at a detector; and processing the sampling and reference signals to determine an oxygen level in the fluid environment based on the sampling signal with reference to the reference signal independent of varying temperature in the fluid environment.

The gas impermeable enclosure can contain a predetermined fixed oxygen number density, partial pressure, or concentration within a medium, and the oxygen number density, partial pressure, or concentration within the gas impermeable enclosure can be greater than 0% and less than or equal to a predetermined limit.

The step of providing a light source can include providing light energy to the sampling probe and reference probe simultaneously from a single LED or Laser light source.

The step of processing the sampling and reference signals can include mixing the sampling signal with the reference signal to identify a phase lag between the sampling and reference signals, and using the phase lag to determine the oxygen level in the fluid environment. This step may also include direct determination of the fluorescent lifetime of the sampling and reference probes or comparing the normalized luminescent decay between the sampling and reference signal to identify relative decay rates.

Both the temperature and pressure of a medium contained in the gas impermeable enclosure can be equilibrated to the temperature and pressure of the fluid environment to provide an accurate reference concentration of oxygen for determination of the concentration of oxygen in the fluid environment.

The method can further include the steps of providing a long-pass filter in front of the detector; for each of the sampling and reference probes, reflecting light from a red LED off the PSP forming the sampling and reference probes, and transmitting the reflect light to the detector to produce a system phase lag signal for the sampling and reference probes; for each of the sampling and reference probes, illuminating the sampling and reference probes with a blue/UV LED to excite the sampling and reference probes to emit phase shifted fluorescent sampling and reference signals transmitted to the detector; and determining a corrected sampling and reference signal for each of the sampling and reference probes by subtracting the fluorescent phase shifted signal of the sampling and reference probes from the respective system phase lag signal. In addition, signals from the sample and reference probes can be transmitted to the detector along respective sampling and reference channels, each of channels can include a shutter, and the shutters can be alternately opened and closed to selectively permit passage of signals through one of the sampling and reference channels while preventing passage of signals along the other of the sampling and reference channels. Further, the corrected reference signal can be subtracted from the corrected sampling signal to determine the oxygen level in the fluid environment.

In accordance with a further aspect of the invention, a method of sensing an oxygen level in a fluid environment is provided. The method comprises obtaining a sampling signal from a sampling luminescent oxygen probe located in the fluid environment; obtaining a reference signal from a reference luminescent oxygen probe located within a gas impermeable enclosure positioned in the fluid environment; providing a predetermined fixed oxygen number density, partial pressure, or concentration of oxygen within a medium contained in the gas impermeable enclosure; equilibrating both a temperature and a pressure of the medium within the gas impermeable enclosure to the temperature and pressure of the fluid environment; receiving the sampling and reference signals at a detector; and processing the sampling and reference signals to determine an oxygen concentration in the fluid environment based on the sampling signal with reference to the reference signal independent of varying temperature or pressure in the fluid environment.

The sampling and reference luminescent oxygen probes can be formed by an ideal PSP.

The determination of the oxygen level can include determining a concentration of oxygen within the fluid environment.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

In accordance with an aspect of the invention, a sensor is provided for monitoring a sensed condition comprising oxygen number density, partial pressure, or concentration in which the effects of varying environmental conditions that could affect the accuracy of the sensed condition are reduced or minimized. In particular, the construction of the sensor includes selection of stable sensor materials in combination with a self-referencing construction for minimizing effects of variations within the measured environment, and within the probe materials, such as temperature, reference condition, photo-degradation, detector noise, or long-term drift, to provide a reliable sensor with substantially improved accuracy in sensing small variations in oxygen number density, partial pressure, or concentration.

In accordance with specific aspects of the invention, a luminescence-based oxygen sensor is described that may include a luminescent oxygen probe comprising a probe molecule having stable calibration and that may have a uniform sensitivity to oxygen number density across a range of temperatures. The sensor additionally includes a self-referencing detection configuration having an in-situ reference probe that provides an in-situ calibration or reference data point for any operating point of the oxygen probe.

The following provides a description of oxygen sensing within the specific context of measuring the number density, partial pressure, or concentration of oxygen in the ullage of a fuel tank, i.e., in the vapors above the fuel in a fuel tank. However, it should be understood that, in accordance with the underlying principles of the invention, the described system for monitoring a fluid may be used in contact with either a gas or a liquid environment, i.e., in a fluid environment. In addition, the present monitoring system may be used to monitor other contained environments such as, for example, a reactor, a processing bath, gas analysis, as well being applicable in water quality analysis, and analysis of dissolved oxygen in fuel, wine, beer or other environments. Hence, the present description should be understood to be non-limiting with regard to the scope of application of the invention.

Figure 1:
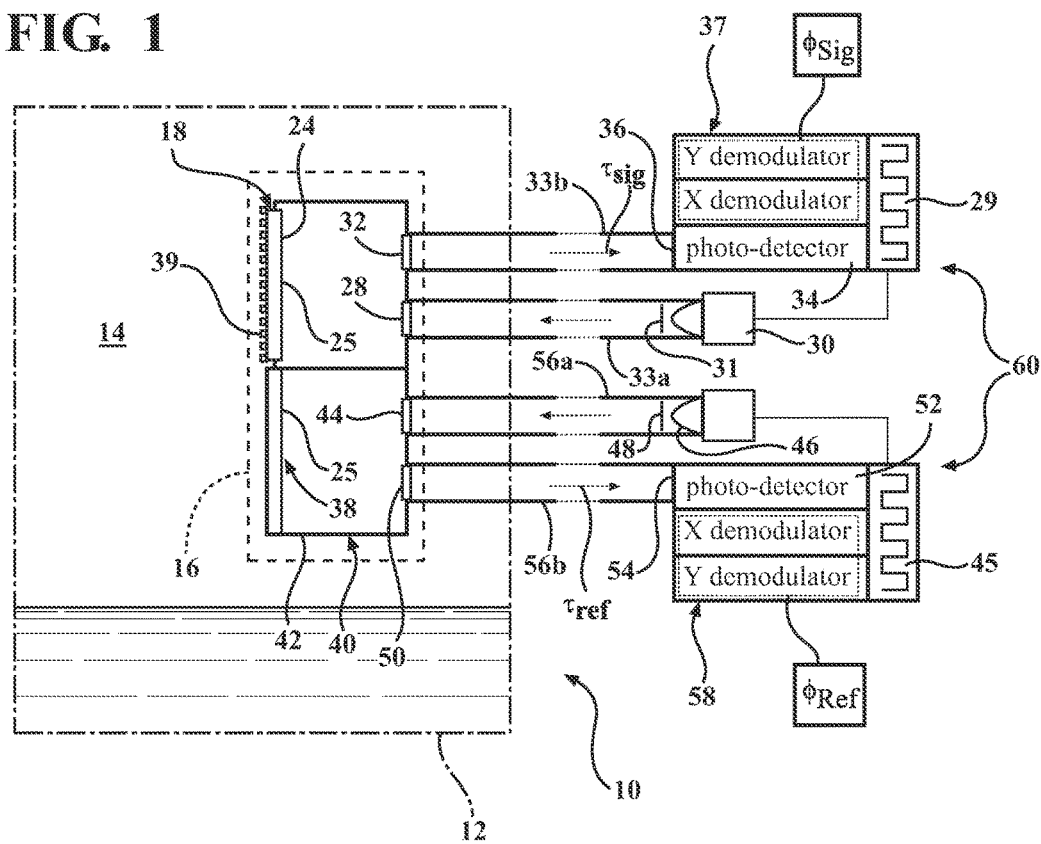
FIG. 1 is a diagrammatic view illustrating a system for monitoring the partial pressure of oxygen in the ullage of a fuel tank in accordance with aspects of the present invention.
Figure 2:
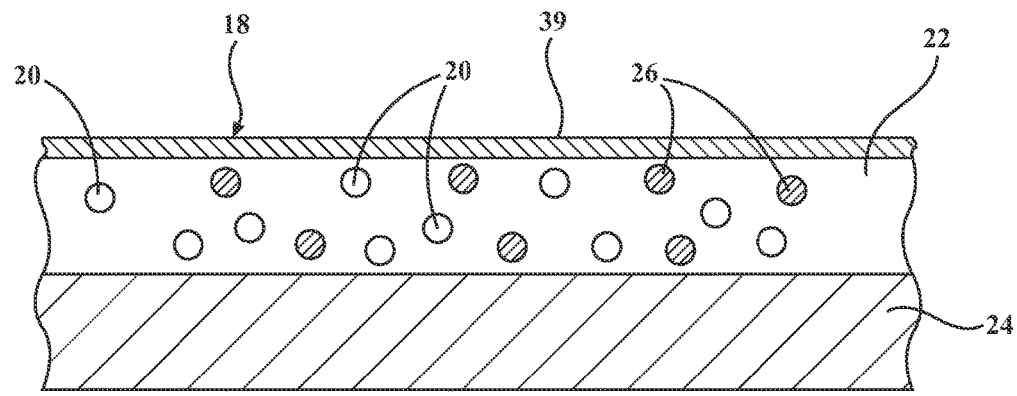
FIG. 2 is a diagrammatic view illustrating a section of a sampling probe structure.

Referring to FIG. 1, a system 10 for monitoring a fluid is illustrated and, in particular, the system 10 comprises a monitoring system for monitoring the number density, partial pressure, or concentration of oxygen in the ullage 14 of a fuel tank 12, such as an aircraft fuel tank. The system 10 includes a sensor head 16 that is located within the ullage 14. The sensor head 16 includes a first luminescent oxygen sampling probe structure 18 that comprises a selected photo-luminescent material, depicted by photo-luminescent molecules (oxygen probe) 20, in an oxygen permeable polymer matrix binder 22 that is coated on a sampling surface 24 of the sensor head 16. The sampling surface 24 can be a transparent surface for permitting transmission of light through the surface 24. The oxygen probe 20 and binder 22 may be provided in the form of a pressure sensitive paint 25, hereinafter referred to as "PSP", which operates on the principle of certain luminescent molecules, i.e., the oxygen probes 20, being sensitive to the presence of oxygen. It should be understood that the use of the terminology "pressure sensitive paint" or "PSP" can broadly include other physical embodiments, such as preformed films or other material characteristics for the combined probe and binder structure described herein.

Generally, when a luminescent molecule absorbs a photon, it is excited to an upper singlet energy state. The molecule then typically recovers to the ground state by the emission of a photon of a longer wavelength. Pressure sensitivity, or in reality oxygen sensitivity, of the luminescent molecules results when an excited luminophore interacts with an oxygen molecule and transfers some of the excited state energy to a vibrational mode of the oxygen molecule. The resulting transition to the ground state is radiationless in a process known as oxygen quenching. The rate at which the quenching process competes with the radiation process is dependent on the number density of oxygen molecules present, with a higher oxygen number density quenching the luminescent molecules more, thus reducing the lifetime of the fluorescence, and therefore, the integrated fluorescent signal. Also, there is a time delay between reception of incoming excitation light and emission from the luminescent molecules and, in the case of a sinusoidal or cyclical excitation light signal, the delay may be evidenced by a phase shift between excitation and emitted light signals, the phase shift being a function of the fluorescence lifetime of the probe, and therefore, the number density of the oxygen molecules present; with a higher number density of oxygen molecules resulting in a shorter lifetime, and therefore, a reduced phase lag.

In the system 10 described herein, a first illumination or light source 28 provides illumination to the PSP 25, such as from an LED 30, or LED array, and a short pass filter 31 may be provided between the LED and the PSP. A first or sampling receptor 32 receives the emission from the PSP 25 for detection at a first detector (photo detector) 34. The emission from the PSP 25 at the first receptor 32 defines a test or sampling signal $\tau_{sig}$ that is transmitted through detector 34 to a processor 60. The detector 34 can be a CCD camera, a photo-multiplier tube, or a photo-diode, and the emission may be filtered through a long-pass filter 36 prior to the first detector 34. The light transmitted to and from the PSP 25 may be transmitted though respective optical fibers 33a, 33b, where the optical fiber 33b and first detector 34 can define a test or sampling channel providing the sampling signal $\tau_{sig}$ to the processor 60.

The fluorescence or output from the photo-luminescent material 20 received at the first receptor 32 provides a proportional indication of the number density, partial pressure, or concentration of oxygen at the sensor head 16. The luminescent signal received from the PSP 25 may be recorded by the detector 34 and converted to number density, partial pressure, or concentration using a previously determined calibration. In practical applications of lifetime-based PSP 25 to determine number density, partial pressure, or concentration, the luminescent lifetime measured from a PSP 25 can be a function of several parameters, in addition to the number density, partial pressure, or concentration of oxygen being measured, including variations in concentration of the luminophore in the PSP. These variations are minimized in the present description by comparing the luminescent lifetime of the PSP 25 at the test or "wind-on" condition with the luminescent lifetime of the PSP 25 at a known reference or "wind-off" condition to provide a normalized basis for the relationship between luminescent lifetime and number density, partial pressure, or concentration of oxygen. The number density, partial pressure, or concentration of oxygen may be alternatively referred to herein by the general term "oxygen level".

In accordance with an aspect of the invention, it has been noted that prior photo-luminescent probe structures generally exhibited a substantial variation in the luminescent output with varying temperature, i.e., a temperature sensitivity. The temperature sensitivity can be generated by two mechanisms including thermal quenching of the luminescent probe 20 and the temperature dependent permeability within the polymer matrix forming the binder 22 that holds the luminescent probe 20. The effects of temperature sensitivity may be seen in FIG. 3 in which lines $T_{A1}$ and $T_{A2}$ illustrate the luminescent output of a prior system including a PSP formed with a polymer matrix having a permeability that exhibits varying permeability with temperature, which can adversely affect the calibration of the prior system. In particular, although lines $T_{A1}$ and $T_{A2}$ show that the variation of emission output with a varying number density, partial pressure, or concentration of oxygen is generally linear at a constant temperature, changes in temperature result in a calibration line of substantially different slope, and thus exhibits a relatively high sensitivity to temperature of about 4% per ° C. This temperature sensitivity typically necessitates obtaining an absolute temperature measurement in order to identify the correct calibration line for determining a number density, partial pressure, or concentration of oxygen. Hence, the temperature sensitivity of the probe has typically increased the complexity of the making an accurate determination of number density, partial pressure, or concentration of oxygen because of the need to account for variations in environmental conditions affecting the probe, specifically temperature.

Figure 3:
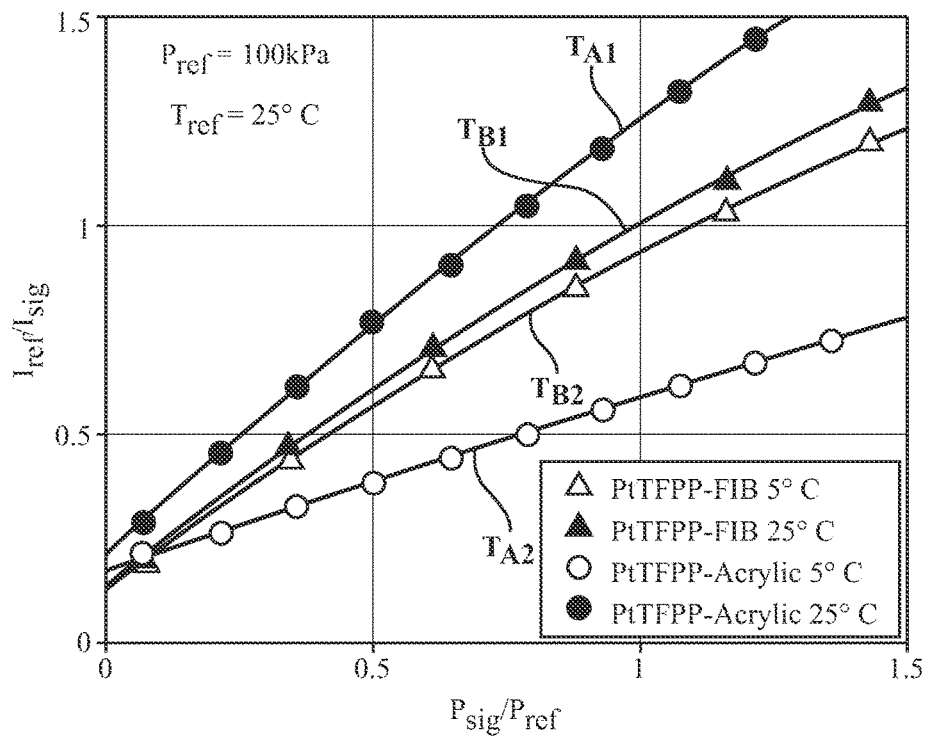
FIG. 3 is a graph illustrating variation in sensitivity of the probe structure of the present invention in comparison to a prior probe structure.

An aspect of the present invention includes implementing a photo-luminescent probe structure including a polymer matrix binder 22 that provides a stable emission output with varying temperature, as may be seen by lines $T_{B1}$ and $T_{B2}$ in FIG. 3, in which the sensitivity to temperature is relatively very small, such as about 0.5% per ° C. Thus, the particular photo-luminescent probe structure selected for the sensor head 16 of the present invention facilitates calibration of the system 10 with varying conditions to provide accurate number density, partial pressure, or oxygen concentration measurements. For example, the prior probe structure represented in FIG. 3 by lines $T_{A1}$, $T_{A2}$ may comprise platinum tetra (pentafluorophenyl) porphine in an acrylic binder, i.e., PtTFPP-Acrylic, whereas the probe structure of the present sensor head 16, represented in FIG. 3 by lines $T_{B1}$, $T_{B2}$, preferably comprises tetra (pentafluorophenyl) porphine (oxygen probe 20) in a fluoro/isopropyl/butyl binder 22, i.e., PtTFPP-FIB. The fluoro/isopropyl/butyl (FIB) binder 22 has stable characteristics in response to temperature changes, wherein oxygen permeability through the binder 22, and thus to the oxygen probe 20, does not vary significantly with temperature. As a result, the output from the probe 20 as a function of oxygen number density is generally linear, exhibiting very little variation with temperature. The present PSP 25, incorporating PtTFPP-FIB, is referred to herein as an ideal PSP in that the response characteristics of the PSP 25 are very stable, and for a given limited range of oxygen number density, exhibits a constant response slope regardless of operating temperature, as is discussed further below. This constant slope behavior of interest is exhibited in FIG. 6, where the data along each isotherm in FIG. 5 has been normalized using the signal acquired at the reference pressure at that temperature. Note that the slope of the calibration curves is nearly identical when the calibration data is displayed in this manner. This "ideal" behavior does not imply insensitivity to temperature, but does show that the slope of the calibration curve is nearly constant at any temperature within a given range. Additionally, as used herein, "ideal PSP" can be defined as any pressure sensitive paint that has a calibration curve that, when normalized using a reference pressure at each temperature, results in a slope that varies by no more than 0.02% per ° C., i.e., defining a "constant slope" calibration curve.

The PtTFPP-FIB probe 20 may be excited by light from the LED 30 having a wavelength of about 530 nm or less, and may correspond to a blue or UV excitation LED 30. The fluorescent emission from the probe 20 may have a longer wavelength of about 550 nm or greater, and may correspond to a red emitted output from the probe 20.

When the oxygen probe 20 is excited by light, there is a generally predicable delay between the time of excitation and the occurrence of an emission of light as the probe 20 returns to the ground state. The resulting delay in the emission from the probe 20 is affected by oxygen quenching, where increasing oxygen number density results in a predictable decrease in the delay of the emission. In a lifetime approach to determining the oxygen partial pressure, as used in the present description of the invention, a phase-locked loop is employed that identifies a phase lag between an excitation illumination from a light source and an emission from the probe 20. Determination of the phase lag is equivalent to determination of the fluorescent lifetime, and alternative methods of determining fluorescent lifetime may be used, as is discussed further below.

Figure 4:
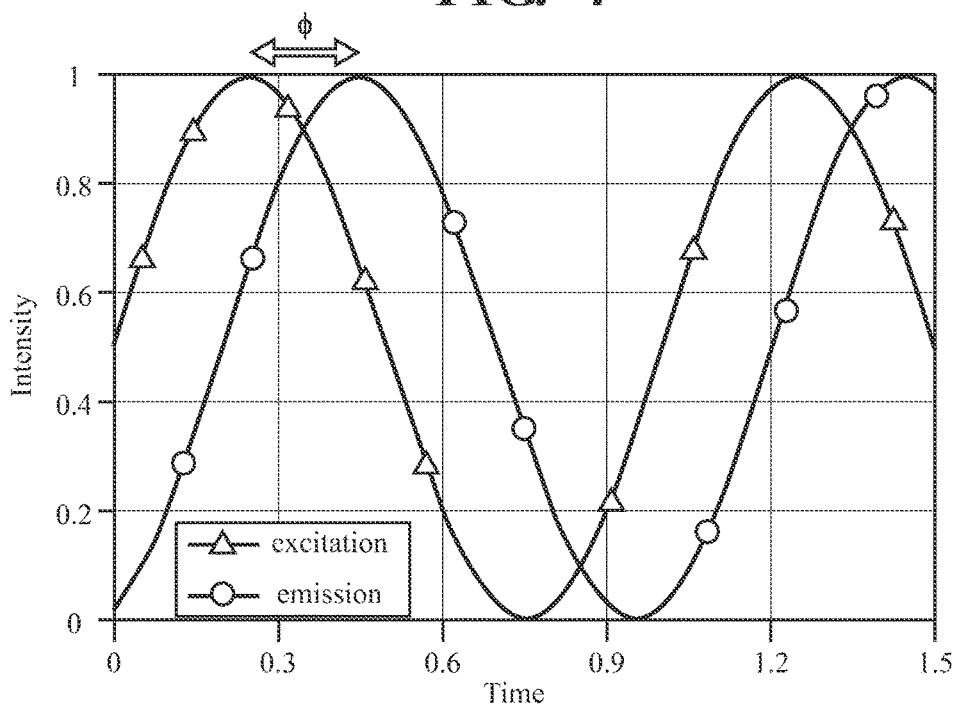
FIG. 4 is a graph illustrating a phase shift between an excitation from a modulated light source and an emission from the probe structure of the present invention.

In the method using the phase-locked loop, the light source 28 is modulated to provide light at a predetermined frequency, such as may be provided by a signal generator 29, and the frequency and phase of the luminescence emitted from the probe 20 relative to the frequency and phase of the modulated excitation light is monitored and processed in a lock-in amplifier 37 (FIG. 1) to determine the phase lag between the excitation and emission signals, as is illustrated in FIG. 4. The phase angle or phase lag is related to the luminescent lifetime of the probe 20. The relationship between the measured phase lag and luminescent lifetime of the probe 20, i.e., the decay time of the luminescence of a single probe assuming a single exponential system, is described by the equation:

$$\tau\omega = \mathrm{Tan}(\phi) \quad (1)$$

where:
$\omega = 2\pi$ times the excitation modulation frequency;
$\phi =$ the phase angle measured by the lock-in amplifier; and
$\tau =$ the luminescent lifetime of the probe.

It may be noted that the empirical result for the exponential decay of multiple probes is similarly described by equation (1).

Theoretically, the lifetime of the probe 20 should be independent of paint thickness, probe concentration, or illumination intensity and the calibration should be invariant over long periods of time. While this assumption may be true for very low concentration probes in solutions with perfect detection schemes, it has not been the case for practical PSPs with real hardware. One method for compensating for variations in characteristics in the sampling probe structure 18 and sampling system that could affect the oxygen measurement is to provide a reference condition to establish a reference lifetime at a known condition, and using this reference condition to anchor the sampling results of the oxygen measurement. The sampling results may be expressed relative to the reference conditions by the following modified Stern-Volmer equation:

$$\frac{\tau_{ref}}{\tau_{sig}} = A(T) + B(T)\frac{P_{sig}}{P_{ref}} \quad (2)$$

where:

$\tau_{sig}$ is the lifetime of the probe 20 during a test or sampling condition;

$\tau_{ref}$ is the lifetime of a reference probe at a known reference condition;

A(T) and B(T) are temperature dependent reaction rate constants $P_{sig}$ is the number density, concentration, or partial pressure of the oxygen to be determined;

$P_{ref}$ is the number density, concentration, or oxygen partial pressure of the reference gas within the impermeable enclosure;

And, from equation (1) above:

$$\tau_{sig} = \frac{\mathrm{Tan}(\phi_{sig})}{\omega}; \quad (3)$$

$$\tau_{ref} = \frac{\mathrm{Tan}(\phi_{ref})}{\omega}; \quad (4)$$

$\phi_{sig}$ is the phase lag of the emission received at the test or sampling detector 32, 36 relative to the modulation of the illumination source 28, 30;

$\phi_{ref}$ is the phase lag of the emission received from the reference probe at a second detector relative to the modulation of a second illumination source;

ω is the frequency of the modulated excitation light, where the first and second illumination sources are operated at the same modulation frequency.

Various factors may affect the emission from the oxygen probe 20 to provide an indication of the oxygen number density, partial pressure, or concentration. In particular the sources of error can include temperature, reference condition, illumination, calibration stability, sedimentation, paint photo-degradation, stray light and camera or detector shot noise. For the present system, factors associated with temperature, reference condition, and detector noise are the main conditions that can affect accuracy of the measured oxygen number density, partial pressure, or concentration. One means of minimizing these errors is to integrate a reference channel into the system 10. The reference channel described herein can preferably compensate for changes in both temperature and detector noise, while also improving measurement accuracy be provided in a reference condition that is close to the desired measurement condition.

In accordance with a further aspect of the invention, the sensor head 16 may be provided with a reference probe structure 38, as seen in FIG. 1. The reference probe structure 38 is preferably located close to the sampling probe structure 18, and may be formed as a connected or integral structure with the sampling probe structure 18, such that the sampling probe structure 18 and the reference probe structure 38 are physically located in the same environment and have the same temperature. The reference probe structure 38 includes a sealed, gas impermeable reference enclosure or cell 40, defined by wall 42, that seals in a quantity of oxygen at a predetermined number density, partial pressure, or concentration. That is, a known fixed number density or concentration of oxygen is maintained in the reference cell 40 to be used as an in-situ reference for determining an oxygen level in the environment. At least a portion of the interior surface of the wall 42 is coated with the PSP (reference PSP) formed of the same PtTFPP-FIB material as is provided for the sampling probe structure 18. The wall 42 defining the enclosure 40 could be formed of glass and may comprise, for example, a sealed Pyrex® enclosure 40.

A second illumination or light source 44 provides illumination to the reference PSP, such as from an LED 46, or LED array, and a short pass filter 48 may be provided between the LED 46 and the reference PSP. A second receptor 50 receives the emission from the reference PSP for detection at a second detector (photo-detector) 52. The emission from the PSP 25 at the second receptor 50 defines a reference signal $\tau_{ref}$ that is transmitted through second detector 52 to the processor 60. The second detector 52 can be a CCD camera, a photo-multiplier tube, or a photo-diode, and the emission may be filtered through a long-pass filter 54 prior to the second detector 52. The light transmitted to and from the PSP may be transmitted though respective optical fibers 56a, 56b, where the optical fiber 56b and second detector 52 can define a reference channel $\tau_{ref}$ providing the reference signal to the processor 60.

The second light source 44 is modulated to provide light at a predetermined modulation frequency, such as a sinusoidal modulation frequency, and the frequency of the luminescence emitted from the reference probe structure 38 is monitored and processed in a lock-in-amplifier 58 to determine the phase lag between the reference excitation and emission signals, and therefore the luminescent lifetime of the reference probe. The second light source 44 is preferably modulated at a frequency that is the same as the modulation frequency for the first light source 28, such as may be provided by a signal generator 45. In this way, the reference probe structure 38 provides the reference lifetime $\tau_{ref}$, i.e., the signal $\tau_{ref}$, at a known reference condition. That is, the reference lifetime $\tau_{ref}$ is obtained from a reference probe structure 38 at a known condition (i.e. oxygen number density, partial pressure, or concentration) to establish an in-situ reference or lifetime in order to produce accurate data, thus providing a self-anchoring detection scheme. The reference probe structure 38 provides a reference phase angle $\phi_{ref}$, i.e., between the frequency modulations of the excitation illumination and the resulting emission, at a known number density, concentration, or partial pressure of oxygen contained in the sealed enclosure 40 and at the same temperature as the sampling probe structure 18, enabling other factors affecting the phase angle that are not associated with the oxygen number density, concentration, or partial pressure of oxygen in the sampling environment to be eliminated.

It may be understood that the components for generating the light signals and receiving and processing the emitted light signals, including the lock-in-amplifiers 37, 58 and signal generators 29, 45 may operate under the control of the processor 60. Additionally, the processor 60 may also include the first and second detectors 34, 52. Also, the first and second sources 28, 44 may be provided in the form of light provided from a Laser, such as Q-switched Laser providing a pulsed output, as may be depicted by elements 30, 46 in FIG. 1. Further, it should be understood that the first and second light sources 28, 44 may be provided with light from a common LED source, as is described further below.

Figure 5:
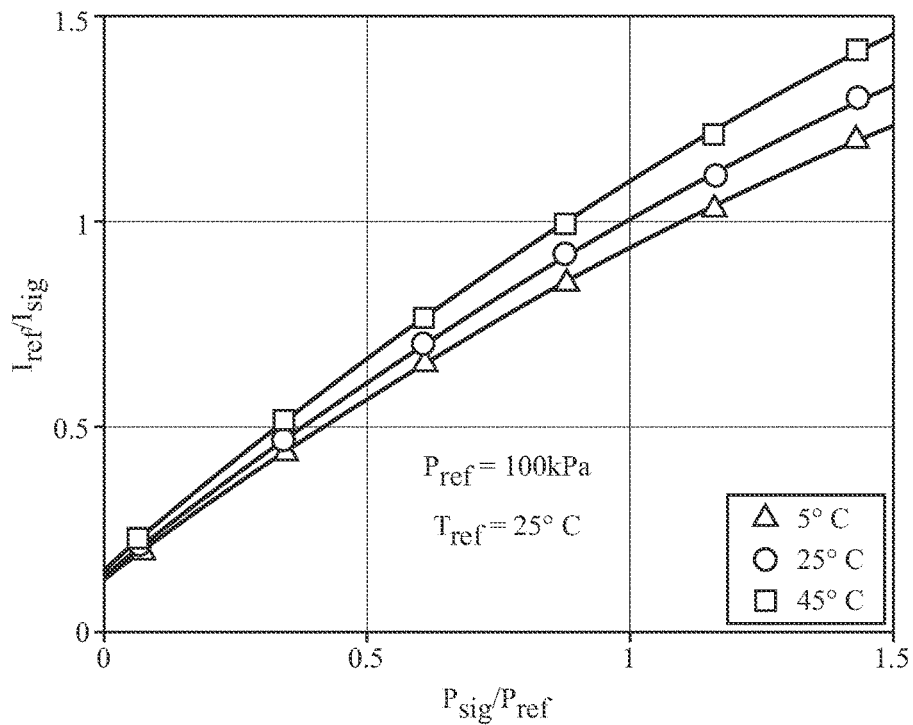
FIG. 5 is a graph illustrating calibration lines for the probe structure of the present invention at different temperatures.

It should be noted that, as discussed above, the temperature sensitivity of PtTFPP-FIB, as used in forming the sampling probe structure 18 and the reference probe structure 38, is generally constant over a wide range of oxygen partial pressures or number densities and has very low temperature sensitivity, thus minimizing thermal errors. This may be seen in FIG. 5 illustrating calibration curves for PtTFPP-FIB normalized at a single pressure and temperature of 100 kPa and 25° C. Furthermore, the implementation of the package that results in the sensor and reference PSP samples being in thermal equilibrium results in a system where the calibration curves may be normalized at each temperature using the given reference pressure (i.e. 100 kPa at each temperature). The resulting calibration plot, shown in FIG. 6, demonstrates that the slope of the calibration curve is essentially identical at each temperature over a wide range of pressures, an "ideal" PSP. This means that there is no need to measure the temperature of the sensor. This may be contrasted with a non-ideal PSP in which an appropriate calibration curve will vary with temperature, i.e., result in a temperature offset affecting sensitivity, and requires that an absolute temperature measurement be provided to identify the correct calibration curve even if a reference cell is used to provide a known reference condition. In summary, the ideal PSP 25 provides a calibration curve that is substantially identical at each temperature, i.e., varies no more that about 0.02% per ° C., whereas a non-ideal PSP provides a calibration curve having a slope that is a function of temperature such that, in addition to a reference condition, an absolute temperature is required to correlate the PSP output to a partial pressure, concentration, or number density of $O_2$.

Figure 6:
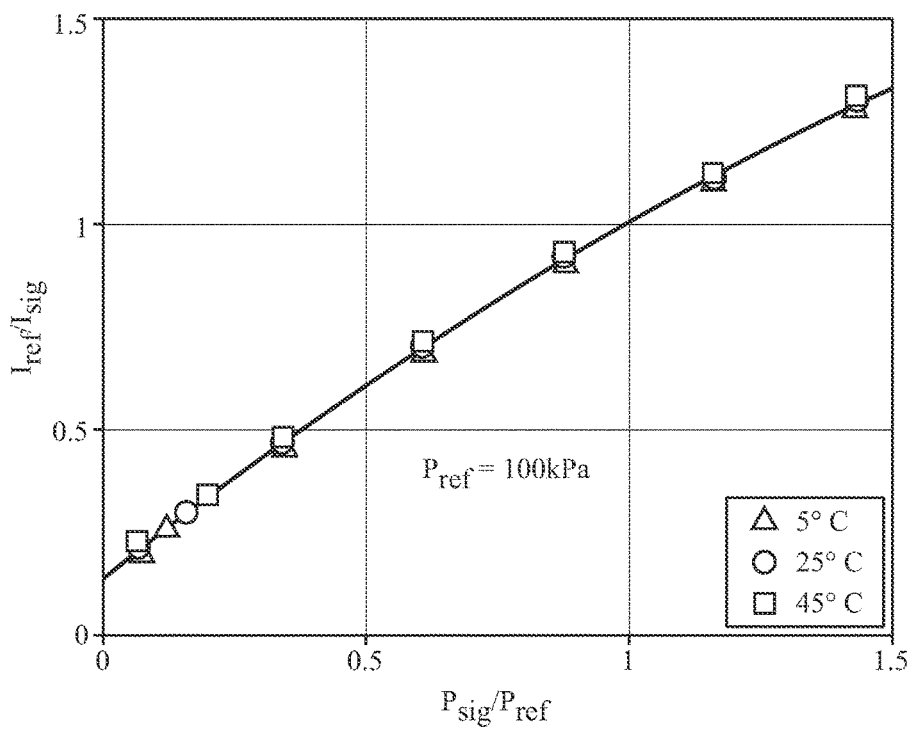
FIG. 6 is a graph illustrating calibration lines similar to the calibration lines of FIG. 5 in which the calibration lines are normalized at each temperature.

Since the reference probe structure 38 is at the same temperature as the sampling probe structure 18, and both the reference probe 38 and sampling probe 18 use the ideal PSP 25, the slope of the calibration curve is independent of temperature. That is, there is no need to measure the absolute temperature, or any temperature, to apply the correct calibration curve, as is shown by calibration curves that are normalized at each temperature, as illustrated in FIG. 6. FIG. 6 illustrates calibration curves for PtTFPP-FIB normalized at 100 kPa at each temperature (5° C., 25° C., 45° C.), in which the calibration lines for the different temperatures substantially overlap each other. Hence, the selected PtTFPP-FIB material of the probe structures 18, 38 provides a high sensitivity system in which the sensitivity is not a function of temperature.

In addition, the use of the present heavily fluorinated polymer, i.e., PtTFPP-FIB, provides a matrix that is substantially immune to attack by singlet oxygen, which is a byproduct of the luminescent quenching process, as well as other chemical attacks. This immunity of the probe structure polymer to chemical attack results in a very stable calibration between the luminescent lifetime and the oxygen partial pressure or number density, which is an essential characteristic for providing a long sensor life-time, as is necessary for applications such as monitoring the ullage in aircraft fuel tanks. Further, the PSP coating on the surface 24 is preferably protected from the fuel in the tank 12 by a screen material 39 that is permeable to oxygen but impermeable to the fuel. Examples of screen material 39 include Tyvek®, Teflon®, silanized alumina, ceramic filters, and FIB may also be utilized as an effective screen material 39. The oxygen in the ullage 14 diffuses through the screen material 39 to the photo-luminescent molecules 20.

Figure 7:
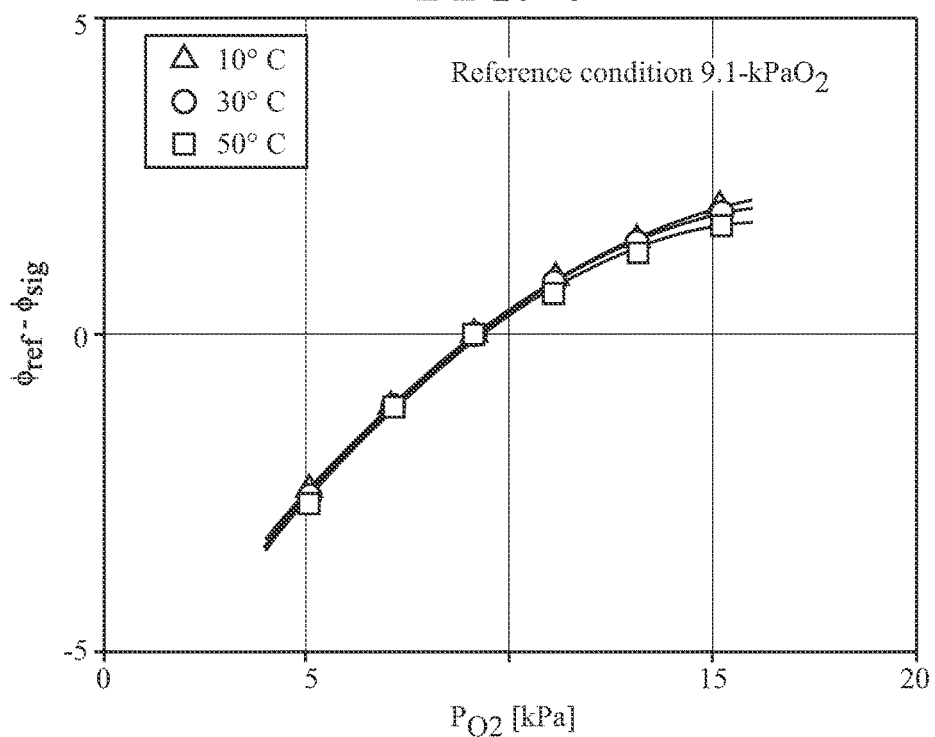
FIG. 7 is a graph illustrating a variation in phase shift difference between a sampling and reference probe with change in oxygen pressure.

It may be noted that, although there is a difference between the sampling phase angle $\phi_{sig}$ and the reference phase angle $\phi_{ref}$, FIG. 7 illustrates that, in an ideal configuration of the sampling and reference probe structures 18, 38, a phase difference between the sampling and reference probe angles is a predictable monotonic function of oxygen pressure or number density. In the illustrated example, the reference probe structure comprises a Pyrex® cell having a PtTFPP-FIB film coated on the inside wall of the cell and containing oxygen at a pressure of 9.1 kPa (i.e. ~9% oxygen concentration at 1 atm.). This reference cell is located in the ullage adjacent to the sampling probe structure 18. The luminescent lifetime of the reference probe structure 38 is detected using a phase-locked-loop that is identical to the phase-locked-loop for detecting the emission from the sampling probe structure 18. If it is assumed that the two probes are in thermal equilibrium, then a measurement of the lifetime of the luminescent sensor in the reference cell, at a known oxygen number density and at the same temperature as the ullage sensing probe is provided. The reference cell then serves as an in-situ reference condition, similar to a pressure tap. Further, since the material of the sampling and reference probe structures is PtTFPP-FIB, the slope of the calibration curve is constant at any temperature within a range of about −40° C. to 50° C., i.e., the probe structures each comprise an ideal sensor, and there is no need to measure the temperature.

In accordance with a further aspect of the invention, it has been observed that errors in the accuracy of the measured number density, partial pressure, or concentration of oxygen can be reduced by utilizing a reference condition in the enclosure 40 that most closely matches the sampling condition in the ullage 14, including providing an oxygen number density of the sealed enclosure 40 at about the same oxygen number density as the sampling pressure, i.e., at the same number density as the number density of oxygen in the ullage 14. An aspect of the invention includes detecting when the number density, concentration, or partial pressure of oxygen in the sampling environment or ullage reaches a predetermined limit for a particular application, wherein the reference number density of oxygen is set at or close to the predetermined limit number density of oxygen in the sampling environment. In the present example in the environment of an aircraft fuel tank, the predetermined limit typically corresponds to a 9% oxygen concentration explosive limit, and the predetermined number density of the oxygen contained in the reference enclosure 40 may be set to correspond to 9% oxygen concentration at ullage flight conditions in order to provide an accurate measurement when the oxygen concentration in the ullage 14 reaches this level. In accordance with a more general aspect of the invention, the predetermined number density can be set to correspond to a concentration of the oxygen in the reference enclosure 40 that is greater than 0% and less than or equal to 9% to thereby provide a number density close to the sampled number density within the ullage 14, with an associated improvement in accuracy.

Figure 8:
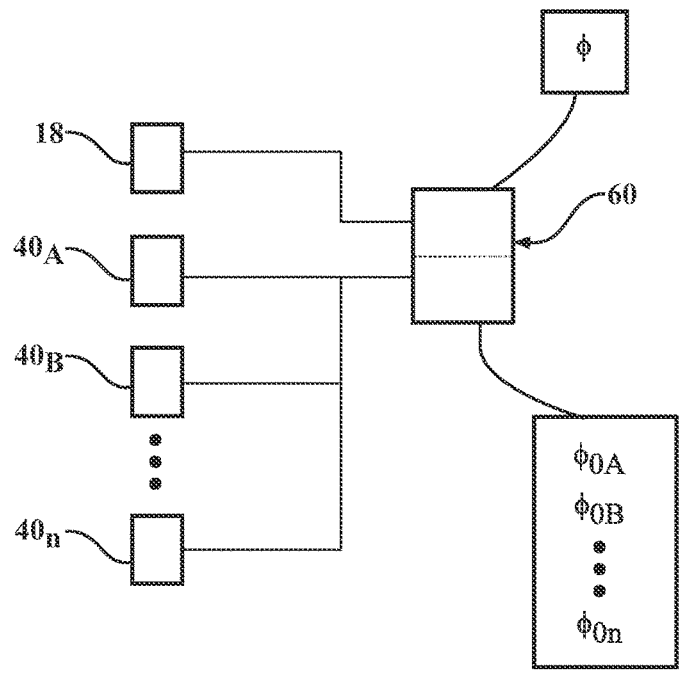
FIG. 8 is a schematic view illustrating an alternative configuration for the system for monitoring the partial pressure of oxygen, including plural reference cells for plural reference probe structures.

Referring to FIG. 8, two or more reference enclosures or cells 40 and associated reference probe structures 38 may be provided, as is depicted by reference cells $40_A, 40_B, \ldots 40_n$. Each of the reference cells $40_A, 40_B, \ldots 40_n$ may be maintained at a respective different number density, partial pressure, or concentration of oxygen to provide accurate readings of the oxygen level in the ullage 14 at different points in the flight path (i.e. taxi, cruse, takeoff, landing), thereby increasing the accuracy of the oxygen number density, partial pressure, or concentration determination throughout the range of operating conditions. It may be understood that the number density in the reference cell 40 is preferably as close as possible to the number density being measured by the sampling probe structure 18. However, since this is typically not practical, the plural reference cells $40_A$, $40_B$, ... $40_n$ can provide at least one cell that has a number density close to the number density in the ullage. Additionally, it may be understood that providing the plural reference cells $40_A$, $40_B$, ... $40_n$ enables formation of a plot or curve, wherein the phase shift associated with a number density in the ullage 14 can fall on interpolated locations between the points provided by reference cells $40_A$, $40_B$, ... $40_n$ to provide relatively accurate values identifying the sampled number density of $O_2$ in the ullage 14.

Additionally, first and second reference probes may be provided at different number densities wherein the first reference probe is at a first number density for triggering a system to change the oxygen number density in the fluid environment, and the second reference probe is at a second number density for triggering the system to discontinue changing the oxygen number density in the fluid environment. In a specific example, one reference cell, e.g., cell $40_A$, may be maintained at a number density that simulates 9% oxygen concentration to trigger an inerting system for purging the ullage 14 and reducing the oxygen, and a second cell $40_B$ may be maintained at a lower oxygen number density to signal that the oxygen concentration is at a predetermined safe level, i.e., at some predetermined concentration less than 9% oxygen, to trigger a deactivation of the inerting system. Such an arrangement could be used to minimize activation of the inerting system, and associated losses, by deactivating the inerting system when the predetermined safe oxygen concentration is present in the ullage 14.

Figure 9:
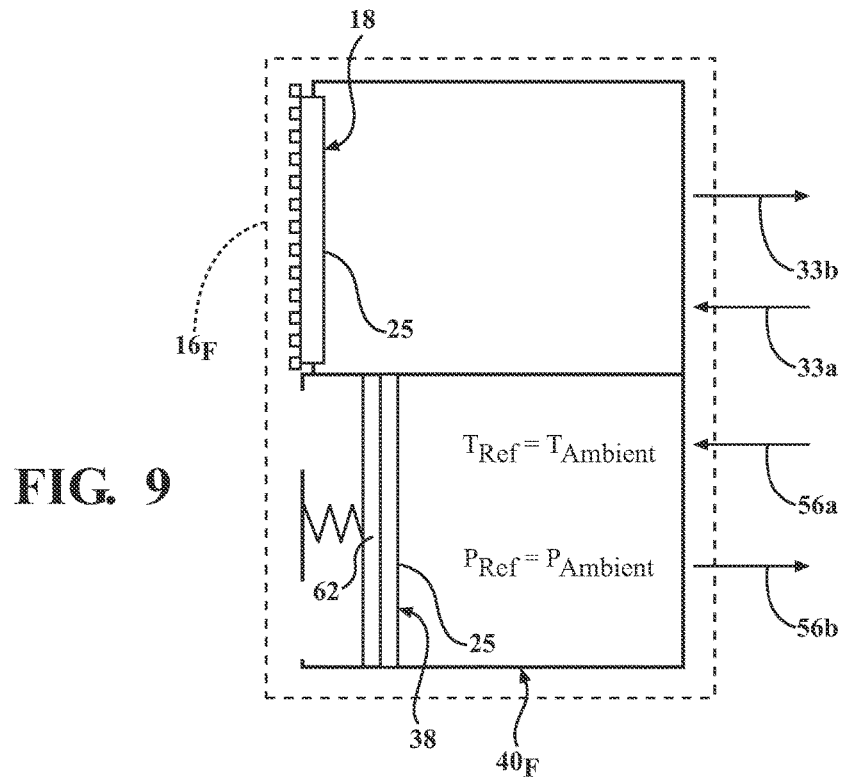
FIG. 9 is a diagrammatic view illustrating a system for monitoring an oxygen level in a system including a reference cell that can equilibrate to an ambient temperature and pressure.

In a further aspect of the invention, a sensor head $16_F$ may be configured to determine the concentration of oxygen in a sampling volume. That is, the sensor head $16_F$ may be constructed as a self-referencing oxygen concentration sensor. Referring to FIG. 9, a floating reference cell $40_F$ may be formed to permit the volume of the reference cell $40_F$ to change with a changing pressure of the surrounding environment, such as in a fuel tank ullage. For example, the reference cell $40_F$ may be formed with a movable wall or piston 62 in which the piston 62 may be free move to regulate the reference cell to the local static pressure. The changing volume of the reference cell $40_F$ permits the pressure of the reference cell $40_F$ to adjust to ambient conditions, while the concentration of the gas in the reference cell $40_F$ remains the same. Since the reference cell $40_F$ is provided with a known $O_2$ concentration, and the temperature and pressure in the reference cell $40_F$ equilibrate to the ambient or local temperature and pressure, the unknown concentration of the $O_2$ outside of the reference cell $40_F$, e.g., in a fuel tank ullage, can be computed by comparing the lifetime of the PSP 25 in the sampling probe structure 10 to the lifetime of the PSP 25 in the reference cell $40_F$. The described sensor head $16_F$ is self-anchoring or self-referencing in that the reference cell $40_F$ can float or equilibrate to the ambient conditions of temperature and pressure, and includes $O_2$ at a known concentration such as 9%. Hence, there is no need to adjust for environmental conditions to obtain the concentration of $O_2$ in the sample (ambient environment).

It should be noted that the described reference cell $40_F$ for the sensor head $16_F$ is very close to an ideal reference channel in that the reference PSP 25 in the reference cell $40_F$ is at the ambient temperature and pressure, and the gas contained in the reference cell $40_F$ is at a known concentration. In addition, as with the sensor head 16 described with reference to FIG. 1, by implementing the above described sensor head $16_F$ with an ideal PSP 25, it is not necessary to adjust the emitted signals from the sampling probe structure 18 and the reference probe structure 38 for temperature in order to obtain an accurate measurement of concentration. Further, the broad aspect of providing a floating reference cell $40_F$ to measure concentration in a sample, as described herein, could be implemented with a non-ideal PSP, but would require an absolute temperature measurement in order to determine the correct calibration curve for the emission of the PSP, i.e. an absolute temperature measurement would be needed to obtain concentration data at any point other than the exact concentration of the reference cell.

Figure 10:
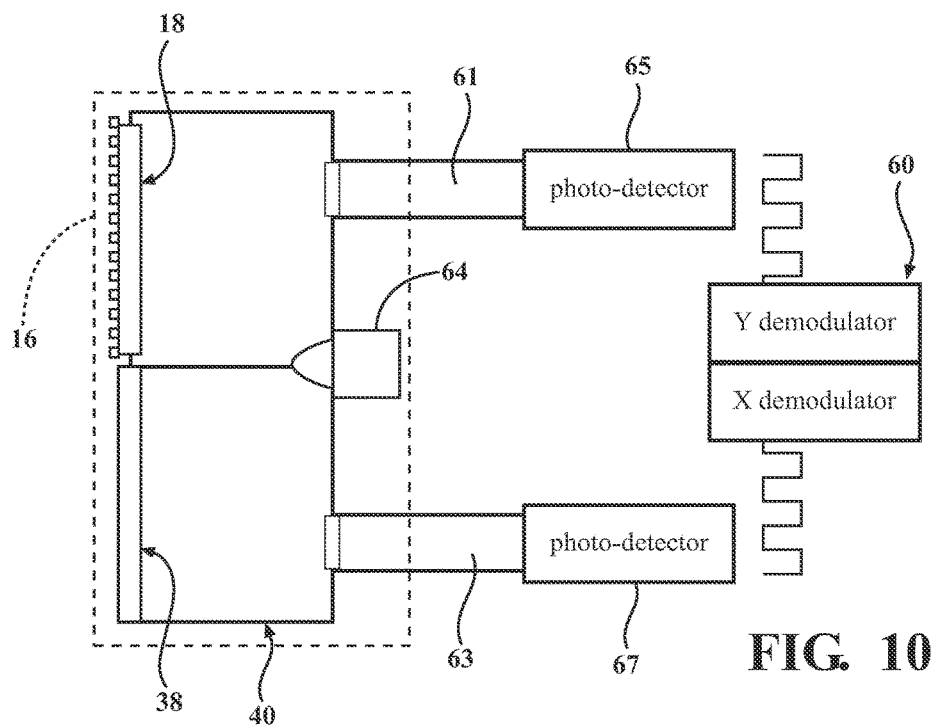
FIG. 10 is a diagrammatic view illustrating a system for monitoring an oxygen level in a system including a single light source for simultaneously illuminating both a sampling and reference probe structure.

FIG. 10 illustrates an alternative aspect of the invention configured to enable comparison of the test or sampling signal $\tau_{sig}$ and the reference signal $\tau_{ref}$ by mixing the two signals, and with minimized drift. In particular, FIG. 10 illustrates a sampling head 16 in which a single light source, defined by LED 64, is connected to provide excitation light energy to both the sampling probe structure 18 and the reference probe structure 38. The resulting fluorescent emissions from the probe structures 18, 38, i.e., signals $\tau_{sig}$ and $\tau_{ref}$, are conveyed via respective channels 61, 63 through detectors 65, 67 to a processor 60 where the signals can be mixed to determine a phase lag of the sampling signal $\tau_{sig}$ relative to the reference signal $\tau_{ref}$. The LED 64 can provide an identical illumination to both of the probe structures 18, 38 to eliminate or substantially reduce error associated with illumination. Also, the light from the LED 64 can provide the same frequency modulated signal to the probe structures 18, 38 simultaneously, such the reference probe signal $\tau_{ref}$ can be viewed as the "excitation" signal and any phase shift in comparing the emitted signals $\tau_{sig}$ and $\tau_{ref}$ is due to a difference in $O_2$ number density between the sampling probe structure 18 and the reference probe structure 40. That is, if the number density of $O_2$ in the sampling probe structure 18 is identical to the number density in the reference probe structure 38, then the phase between the two signals will be zero. However, a phase that is plus or minus from zero phase can indicate an $O_2$ number density that is higher or lower than the $O_2$ at the reference condition in the reference probe structure 40. Additionally, it should be noted that the arrangement of FIG. 10 for providing a single modulated light signal to the sampling and reference probe structures 18, 38 could be implemented in the sampling head $16_F$ described above with reference to FIG. 9 for determining $O_2$ concentration.

In accordance with a further aspect of the invention, a zero point is determined for use in calibrating the phase locked loop, and is provided as a self-calibrating function of the system. In particular, it may be understood that over a period of time there is always some phase shift between the excitation signal and the detected response signal from the PSP that may be attributed to characteristics of the system 10, i.e., a system phase lag not attributed to the phase lag associated with the fluorescence from the PSP. The system illustrated in FIG. 11 provides an alternative configuration for the sampling head that permits the system to identify a zero point for the phase locked loop in order to provide an output that is corrected for system phase lag, as is described in greater detail below.

Figure 11:
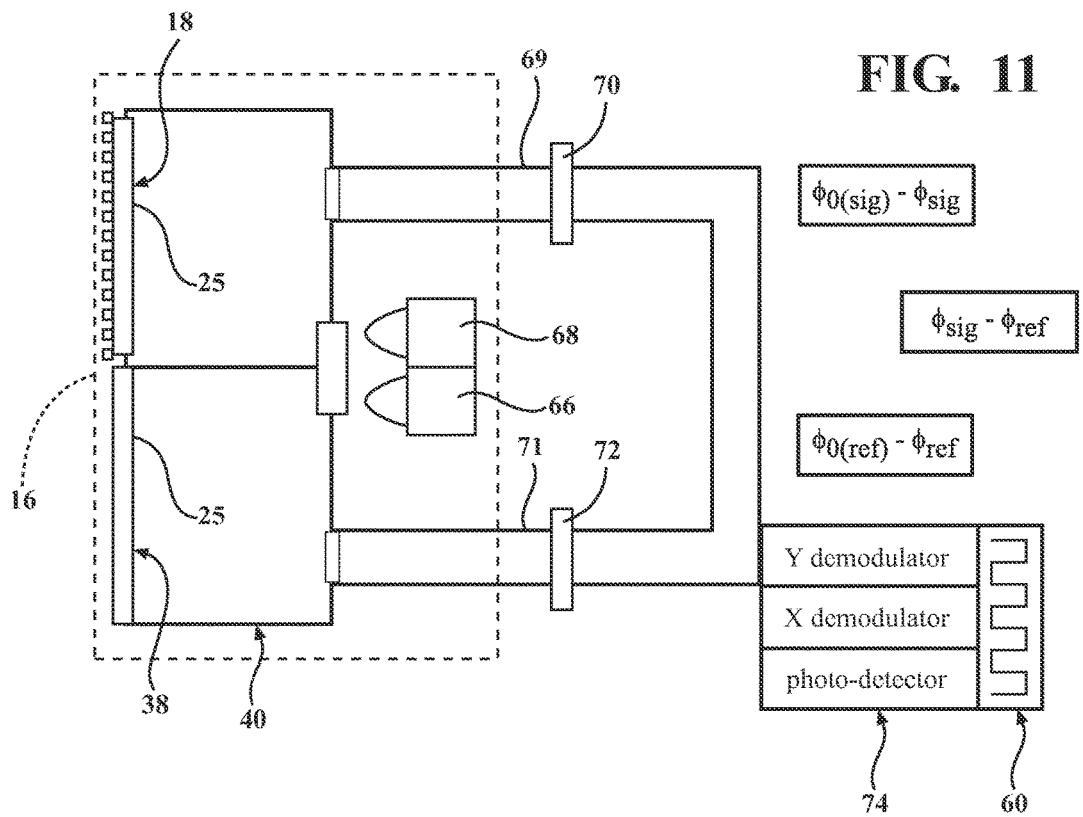
FIG. 11 is a diagrammatic view illustrating a system for monitoring an oxygen level in a system including a self-calibrating arrangement for the system.

FIG. 11 illustrates providing an excitation LED 66, that may be a blue or UV LED, and a calibration LED 68, such as a red LED. The LEDs 66, 68 can be connected to both the sampling and reference probe structures 18, 38, such that each LED 66, 68 can be selectively activated to provide light to both probe structures 18, 38 simultaneously. As noted above, the PSP 25 can operate to emit in the red frequency of light, such that the red LED will not excite the PSP 25 to generate a phase shifted luminescent output. However, the light from the red LED is operating near the emission peak of the PSP 25 and can be reflected off the PSP 25 to provide a light signal that can pass through the long-pass filter in front of the detector and into the photo-detector 74. A system phase shift can be detected between the excitation signal, i.e., an electrical drive signal from the phase locked loop to the red LED 68, and the detector signal, i.e., the signal generated by reflected red light passing to the detector 74. In order to separately calibrate the sampling and reference channels 69, 71 of the system, the channels 69, 71 are provided with respective shutters 70, 72 which can alternately shutter the channels 69, 71 for selectively detecting signals from the sampling and reference probe structures 18, 38.

The system can be operated through a sequence of steps to obtain a zero corrected phase shift. First, the red LED 68 can be energized with the reference channel shutter 72 open and the sampling channel shutter 70 closed. The phase shift between the excitation signal provided to the red LED 68 and the detector 74 signal generated by the reflected red light at the detector is a system phase shift $\phi_{0(ref)}$ for the reference channel 71. Next, operation of the red LED 68 is discontinued and the blue/UV LED 66 is energized with the same shutter configuration, and a resulting reference phase lag $\phi_{ref}$ corresponds to the phase lag of the PSP fluorescence at the reference probe structure 38 from the excitation of the blue LED 66. A corrected reference phase lag $\phi_{ref'}$ is calculated as $\phi_{ref'} = \phi_{0(ref)} - \phi_{ref}$.

Subsequently, the red LED 68 can be energized with the sampling channel shutter 70 open and the reference channel shutter 72 closed. The phase shift between the excitation signal provided to the red LED 68 and the detector signal generated by the reflected red light at the detector 74 is a system phase shift $\phi_{0(sig)}$ for the sampling channel 69. Next, operation of the red LED 68 is discontinued and the blue/UV LED 66 is energized with the same shutter configuration, and a resulting sampling phase lag $\phi_{sig}$ corresponds to the phase lag of the PSP fluorescence sampling probe structure 18 from the excitation of the blue LED 66. A corrected adjusted sampling phase lag $\phi_{sig'}$ is calculated as $\phi_{sig'} = \phi_{0(sig)} - \phi_{sig}$. Finally, a corrected or calibrated phase lag $\phi_{SIG}$, corrected for the system phase lag and anchored to the reference cell, is provided by $\phi_{SIG} = \phi_{sig'} - \phi_{ref'}$.

By providing the present oxygen monitoring system 10 it is possible to provide improved safety in the monitoring of fuel tank ullage, which can be of critical importance in aircraft fuel tanks. In particular, the present system can provide a minimum accuracy of 0.25% oxygen by volume at sea level (approximately 50 Pa $O_2$ absolute) and provide a response time of 10 seconds or better. Further, the probe of the present system can operate over a temperature range of at least −40° C. to 50° C., and operate in a pressure range spanning at least between sea level to 50,000 feet.

Figure 12:
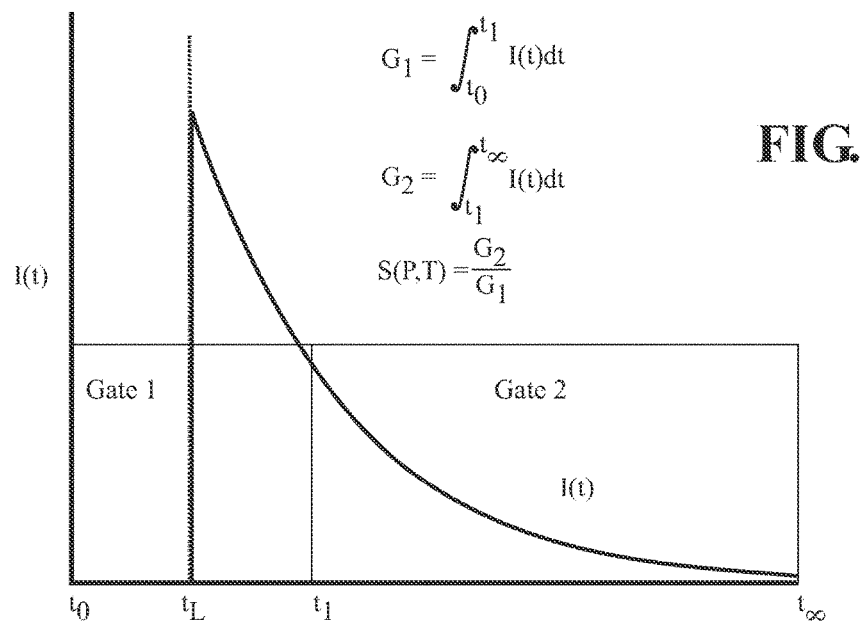
FIG. 12 is a graphical illustration of a further lifetime detection scheme for the probe structure.

Referring to FIG. 12, an alternative method of processing the signals from the sampling and reference probe structures 18, 38 for determining the fluorescence lifetime is illustrated. In the illustrated approach, two gate signals are defined, i.e., Gate 1($G_1$) and Gate 2 ($G_2$), where:

$$G_1 = \int I \omega dt \quad (5)$$

$$G_2 = \int I \omega dt \quad (6)$$

In order to obtain the Gate 1 ($G_1$) and Gate 2 ($G_2$) signals, a trigger fires at time $t_0$ to trigger a Laser lamp and a detector, such as can be provided by a Laser located in the configuration of FIG. 10, and corresponding to element 64, and the detector can be provided by a camera, photo-multiplier tube, or photo-diode corresponding to elements 65, 67. A trigger sync signal can then fire at time $t_L$ to provide a pulsed signal from the Laser 64. The detected probe fluorescence is integrated, and a frame shift at time $t_1$ defines an end to the Gate 1 ($G_1$) integration where the effective Gate 1 ($G_1$) integration is defined between $t_1$-$t_L$, as can be seen graphically in FIG. 12. The duration of Gate 1 is approximately 2-6 μsec. Gate 2 ($G_2$) integrates the remainder of the probe fluorescence from $t_1$ to the end of the fluorescence, such that the Gate 2 ($G_2$) shutter is set by the probe lifetime. It may be noted that the integration of the signal in Gate 1 and Gate 2 can be accomplished directly by a frame transfer camera, as is depicted by FIG. 12. Other similar approaches may also be used including using a gated integrator and box-car averager, which can perform the same as shown in FIG. 12 using an input from a photo-multiplier or a photo-diode. Alternatively, the integration of the signal can be accomplished digitally by digitizing the decay curve signal in time and integrating digitally, such as by using a fast camera, photo-multiplier, or photo-diode, where the decay signal can be digitized and the integrations can be performed numerically. The ratio of Gate 2 to Gate 1 is:

$$S(P, T) = \frac{G_1}{G_2} \quad (7)$$

which provides an indirect measure of the lifetime of the fluorescence, similar to the sampling and reference signals $\tau_{sig}, \tau_{ref}$, i.e., the fluorescence lifetime ($\tau$), described with reference to the phase-locked loop approach described above. The ratio of $G_2$ to $G_1$ will change as the lifetime of the fluorescence changes, such that the relation described by equation (7) is essentially an alternative way of measuring the quantity described by equation (1) above for the phase-locked loop, and the remaining analysis for the two-gate lifetime approach of FIG. 12 can be identical to that described for the phase-locked loop approach. In other words, the ratio of $G_2$ to $G_1$ corresponds closely to the phase lag as it is related to the quantity $\tau$ by equation (1), and a mathematical relationship of the ratio of $G_2$ to $G_1$ as a function of $\tau$ could be implemented wherein, once the value of $\tau$ is obtained from $G_1$ and $G_2$, the remaining relationships and/or calculations are directly applicable from the phase-locked loop approach. Alternatively, it may be noted that the digitized decay versus time curve could be used in a direct curve fit approach, wherein the fluorescence lifetime ($\tau$) can be identified by fitting a single exponential directly to the decay versus time curve depicted in FIG. 12, and can thereby provide a direct indication or value of $\tau$ that can be used in further analysis.

It should be understood that, in essence, a value for the fluorescence lifetime ($\tau$) is obtained, which is a quantity that is sensitive to oxygen number density. This fluorescence lifetime can be determined by various approaches described herein, including using phase lag, gated lifetime, or direct curve fit approaches. Once the fluorescence lifetime ($\tau$) is known, this quantity can be used to infer oxygen number density, and the data can be corrected by using a measurement of fluorescence lifetime ($\tau$) obtained at a reference condition.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oxygen number density or concentration sensor in a fluid environment, the sensor including:
   a sampling luminescent oxygen probe located in the fluid environment;
   at least one gas impermeable enclosure located in the fluid environment and a reference luminescent oxygen probe located within the gas impermeable enclosure, wherein the sampling and reference luminescent oxygen probes are formed by an ideal pressure sensitive paint (PSP);
   a predetermined fixed oxygen number density within a medium contained in the gas impermeable enclosure, the oxygen number density within the gas impermeable enclosure is greater than 0% and less than or equal to a predetermined limit;
   an illumination source providing light energy to the sampling probe and the reference probe;
   a detector receiving signals corresponding to luminescent emissions of the sampling and reference probes; and
   a processor determining a number density of oxygen in the fluid environment from a signal generated at the sampling probe with reference to an oxygen number density dependent signal generated at the reference probe, wherein the processor mixes the signals from the sampling and reference probes to identify the number density of oxygen in the fluid environment based on a luminescent lifetime comparison or phase lag between the signals from the sampling and reference probes.

2. The system of claim 1, wherein the illumination source includes an LED provided to each of the sampling probe and the reference probe, and the detector includes a first detector receiving a luminescent emission of the sampling probe, and a second detector receiving a luminescent emission of the reference probe.

3. An oxygen number density or concentration sensor in a fluid environment, the sensor including:
   a sampling luminescent oxygen probe located in the fluid environment;
   a gas impermeable enclosure located in the fluid environment and a reference luminescent oxygen probe located within the gas impermeable enclosure, wherein the sampling and reference luminescent oxygen probes are formed by an ideal pressure sensitive paint (PSP);
   a predetermined fixed oxygen number density within a medium contained in the gas impermeable enclosure, the oxygen number density within the gas impermeable enclosure is greater than 0% and less than or equal to a predetermined limit;
   an illumination source providing light energy to the sampling probe and the reference probe;
   a detector receiving signals corresponding to luminescent emissions of the sampling and reference probes;
   a processor determining a number density of oxygen in the fluid environment from a signal generated at the sampling probe with reference to an oxygen number density dependent signal generated at the reference probe; and
   wherein the illumination source includes a red LED and a blue LED, and the red and blue LEDs provide light energy to both the sampling and the reference probes and wherein the blue LED is used to create a fluorescent emission from the sampling and reference probes corresponding to an oxygen quenching at each of the probes, and the red LED provides a reflected light signal from the sampling and reference probes that is transmitted to the detector through a long-pass filter to eliminate a system phase lag not associated with fluorescence from the sampling and reference probes.

4. The sensor of claim 3, including a sampling channel from the sampling probe to the detector and a reference channel from the reference probe to the detector, each of the sampling channel and the reference channel including a shutter for selectively controlling passage of signals from the sampling and reference probes to the detector.

5. An oxygen number density or concentration sensor in a fluid environment, the sensor including:
   a sampling luminescent oxygen probe located in the fluid environment;
   a gas impermeable enclosure located in the fluid environment and a reference luminescent oxygen probe located within the gas impermeable enclosure, wherein the sampling and reference luminescent oxygen probes are formed by an ideal pressure sensitive paint (PSP);
   a predetermined fixed oxygen number density within a medium contained in the gas impermeable enclosure, the oxygen number density within the gas impermeable enclosure is greater than 0% and less than or equal to a predetermined limit;
   an illumination source providing light energy to the sampling probe and the reference probe;
   a detector receiving signals corresponding to luminescent emissions of the sampling and reference probes;
   a processor determining a number density of oxygen in the fluid environment from a signal generated at the sampling probe with reference to an oxygen number density dependent signal generated at the reference probe; and
   wherein the reference probe comprises a variable volume cell that varies a pressure within the gas impermeable enclosure to equilibrate to a pressure in the fluid environment.

6. An oxygen number density or concentration sensor in a fluid environment, the sensor including:
   a sampling luminescent oxygen probe located in the fluid environment;
   at least one gas impermeable enclosure located in the fluid environment and a reference luminescent oxygen probe located within the gas impermeable enclosure, wherein the sampling and reference luminescent oxygen probes are formed by an ideal pressure sensitive paint (PSP);
   a predetermined fixed oxygen number density within a medium contained in the gas impermeable enclosure, the oxygen number density within the gas impermeable enclosure is greater than 0% and less than or equal to a predetermined limit;
   an illumination source providing light energy to the sampling probe and the reference probe;
   a detector receiving signals corresponding to luminescent emissions of the sampling and reference probes; and
   a processor determining a number density of oxygen in the fluid environment from a signal generated at the sampling probe with reference to an oxygen number density dependent signal generated at the reference probe;
   wherein said at least one gas impermeable enclosure including at least two separate gas impermeable enclosures and at least two reference luminescent oxygen probes enclosed in respective ones of said separate gas impermeable enclosures, each of the gas impermeable enclosures containing oxygen at respective different number densities or concentrations and used as a reference for the signal generated at the sampling probe.

7. The system of claim 6, wherein a first of the reference probes is at a first number density or concentration for triggering a system to change the oxygen level in the fluid environment, and a second of the reference probe is at a second number density or concentration for triggering the system to discontinue changing the oxygen level in the fluid environment.

8. A method of sensing an oxygen level in a fluid environment, the method comprising:
obtaining a sampling signal from a sampling luminescent oxygen probe located in the fluid environment;
obtaining a reference signal from a reference luminescent oxygen probe located within a gas impermeable enclosure positioned in the fluid environment, wherein the sampling and reference luminescent oxygen probes are formed by an ideal pressure sensitive paint (PSP);
providing a light source modulated at a predetermined frequency to the sampling and reference probes;
receiving the sampling and reference signals at a detector; and
processing the sampling and reference signals to determine an oxygen level in the fluid environment based on the sampling signal with reference to the reference signal independent of varying temperature in the fluid environment;
including equilibrating both the temperature and pressure of a medium contained in the gas impermeable enclosure to the temperature and pressure of the fluid environment to provide a determination of the concentration of oxygen in the fluid environment.

9. The method of claim 8, wherein the gas impermeable enclosure contains a predetermined fixed oxygen number density or concentration within a medium, the oxygen number density or concentration within the gas impermeable enclosure is greater than 0% and less than or equal to a predetermined limit.

10. The method of claim 8, wherein providing a light source includes providing light energy to the sampling probe and reference probe simultaneously from a single LED or Laser light source.

11. The method of claim 10, wherein the light source is a pulsed Laser and the sampling and reference signals are converted to a probe lifetime using multi-gate integration or direct fitting of a decay curve corresponding to fluorescent decay of the probe.

12. The method of claim 8, wherein processing the sampling and reference signals includes mixing the sampling signal with the reference signal to identify a phase lag or lifetime difference between the sampling and reference signals, and using the phase lag or lifetime difference to determine the oxygen level in the fluid environment.

13. The method of claim 8, further including:
providing a long-pass filter in front of the detector;
for each of the sampling and reference probes, reflecting light from a red LED off the PSP forming the sampling and reference probes, and transmitting the reflect light to the detector to produce a system phase lag signal for the sampling and reference probes;
for each of the sampling and reference probes, illuminating the sampling and reference probes with a blue LED or UV light to excite the sampling and reference probes to emit phase shifted fluorescent sampling and reference signals in the red light spectrum transmitted to the detector; and
determining a corrected sampling and reference signal for each of the sampling and reference probes by subtracting the fluorescent phase shifted signal of the sampling and reference probes from the respective system phase lag signal.

14. The method of claim 13, wherein signals from the sample and reference probes are transmitted to the detector along respective sampling and reference channels, each of channels including a shutter, and the shutters are alternately opened and closed to selectively permit passage of signals through one of the sampling and reference channels while preventing passage of signals along the other of the sampling and reference channels.

15. The method of claim 13, including subtracting the corrected reference signal from the corrected sampling signal to determine the oxygen level in the fluid environment.

16. A method of sensing an oxygen level in a fluid environment, the method comprising:
obtaining a sampling signal from a sampling luminescent oxygen probe located in the fluid environment;
obtaining a reference signal from a reference luminescent oxygen probe located within a gas impermeable enclosure positioned in the fluid environment;
providing a predetermined fixed oxygen number density or concentration of oxygen within a medium contained in the gas impermeable enclosure;
equilibrating both a temperature and a pressure of the medium within the gas impermeable enclosure to the temperature and pressure of the fluid environment;
receiving the sampling and reference signals at a detector; and
processing the sampling and reference signals to determine an oxygen level in the fluid environment based on the sampling signal with reference to the reference signal independent of varying temperature in the fluid environment.

17. The method of claim 16, wherein the sampling and reference luminescent oxygen probes are formed by an ideal pressure sensitive paint (PSP).

18. The method of claim 16, wherein the determination of the oxygen level includes determining a concentration of oxygen within the fluid environment.

* * * * *

UNITED STATES PATENT AND TRADEMARK OFFICE
CERTIFICATE OF CORRECTION

PATENT NO. : 9,709,499 B1
APPLICATION NO. : 14/484870
DATED : July 18, 2017
INVENTOR(S) : Jimmy W. Crafton et al.

It is certified that error appears in the above-identified patent and that said Letters Patent is hereby corrected as shown below:

In the Specification

In the Description:

Column 6, Line 44, "PSP 25 may be transmitted though respective optical fibers" should read --PSP 25 may be transmitted through respective optical fibers--

Column 10, Line 24, "the PSP may be transmitted though respective optical fibers" should read --the PSP may be transmitted through respective optical fibers--

Column 12, Line 65, "points in the flight path (i.e. taxi, cruse, takeoff, landing" should read --points in the flight path (i.e. taxi, cruise, takeoff, landing--

Column 13, Line 44, "piston 62 in which the piston 62 may be free move to" should read --piston 62 in which the piston 62 may be free to move to--

Column 14, Line 34, "18, 38 simultaneously, such the reference probe signal" should read --18, 38 simultaneously, such that the reference probe signal--

Column 15, Lines 64-67, "$G_1 = \int I \omega dt$ (5) $G_2 = \int I \omega dt$ (6)"

should read --$G_1 = \int_{t_0}^{t_1} I(t) dt$ (5) $G_2 = \int_{t_1}^{\infty} I(t) dt$ (6)--

Signed and Sealed this
Seventh Day of August, 2018

Andrei Iancu
*Director of the United States Patent and Trademark Office*